United States Patent
Kim et al.

(10) Patent No.: US 11,030,953 B2
(45) Date of Patent: *Jun. 8, 2021

(54) PIXEL AND ORGANIC LIGHT EMITTING DISPLAY DEVICE HAVING THE SAME

(71) Applicant: SAMSUNG DISPLAY CO., LTD., Yongin-si (KR)

(72) Inventors: Dongwoo Kim, Suwon-si (KR); Sunghwan Kim, Yongin-si (KR); Kyoungju Shin, Hwaseong-si (KR); Cheol-gon Lee, Suwon-si (KR); Sang-uk Lim, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/869,789

(22) Filed: May 8, 2020

(65) Prior Publication Data
US 2020/0265782 A1     Aug. 20, 2020

Related U.S. Application Data

(62) Division of application No. 15/704,578, filed on Sep. 14, 2017, now Pat. No. 10,650,739.

(30) Foreign Application Priority Data

Mar. 30, 2017   (KR) .......................... 10-2017-0040936

(51) Int. Cl.
*G09G 3/3233*     (2016.01)
*H01L 27/32*      (2006.01)
(Continued)

(52) U.S. Cl.
CPC ......... *G09G 3/3233* (2013.01); *G09G 3/3266* (2013.01); *G09G 3/3283* (2013.01);
(Continued)

(58) Field of Classification Search
CPC .. G09G 3/3233; G09G 3/3266; G09G 3/3283; G09G 2300/0861;
(Continued)

(56) References Cited

U.S. PATENT DOCUMENTS

2012/0062536 A1   3/2012   Park
2015/0035448 A1   2/2015   Wang
(Continued)

FOREIGN PATENT DOCUMENTS

KR      1020120138924      12/2012

*Primary Examiner* — Abhishek Sarma
(74) *Attorney, Agent, or Firm* — F. Chau & Associates, LLC

(57) ABSTRACT

An organic light emitting display device includes a plurality of pixels. Each of the pixels includes an organic light emitting diode, first to third transistors, a storage capacitor, and a first capacitor. The second transistor includes a gate electrode receiving a first scan signal, a first electrode receiving a data signal, and a second electrode connected to a first electrode of the first transistor. The third transistor includes a gate electrode receiving a second scan signal, a first electrode connected to a second electrode of the first transistor, and a second electrode connected to a gate electrode of the first transistor. The storage capacitor includes a first electrode receiving a power voltage and a second electrode connected to the gate electrode of the first transistor. The first capacitor includes a first electrode connected to the gate electrode of the third transistor and a second electrode receiving the power voltage.

20 Claims, 12 Drawing Sheets

(51) Int. Cl.
  *G09G 3/3266* (2016.01)
  *G09G 3/3283* (2016.01)
  *H01L 27/12* (2006.01)
  *H01L 29/786* (2006.01)

(52) U.S. Cl.
  CPC ...... *H01L 27/1222* (2013.01); *H01L 27/3265* (2013.01); *H01L 27/3276* (2013.01); *G09G 2300/0426* (2013.01); *G09G 2300/0819* (2013.01); *G09G 2300/0823* (2013.01); *G09G 2300/0852* (2013.01); *G09G 2300/0861* (2013.01); *G09G 2320/0214* (2013.01); *G09G 2320/0219* (2013.01); *G09G 2320/0238* (2013.01); *H01L 27/124* (2013.01); *H01L 27/1225* (2013.01); *H01L 27/1255* (2013.01); *H01L 27/3262* (2013.01); *H01L 29/7869* (2013.01); *H01L 29/78675* (2013.01)

(58) Field of Classification Search
  CPC ... G09G 2320/0219; G09G 2320/0214; G09G 2300/0426; G09G 2300/0852; G09G 2320/0238; G09G 2300/0823; G09G 2300/0819; H01L 27/1222; H01L 27/3276; H01L 27/3265; H01L 27/1225; H01L 27/124; H01L 27/1255; H01L 29/7869; H01L 29/78675; H01L 27/3262
  See application file for complete search history.

(56) References Cited

U.S. PATENT DOCUMENTS

2016/0379570 A1  12/2016  Lee et al.
2016/0379571 A1  12/2016  Kim et al.
2018/0286307 A1  10/2018  Kim et al.

PIXEL AND ORGANIC LIGHT EMITTING DISPLAY DEVICE HAVING THE SAME

CROSS REFERENCE TO RELATED APPLICATION

This application is a divisional of U.S. application Ser. No. 15/704,578, filed on Sep. 14, 2017 in the U.S. Patent and Trademark Office, which claims priority under 35 U.S.C. § 119 to Korean Patent Application No. 10-2017-0040936, filed on Mar. 30, 2017 in the Korean intellectual Property Office, the disclosure of which is incorporated by reference herein in its entirety.

TECHNICAL FIELD

Exemplary embodiments of the inventive concept relate to display devices. More particularly, exemplary embodiments of the inventive concept relate to a pixel and an organic light emitting display device having the pixel.

DISCUSSION OF RELATED ART

A display device displays an image using pixels that emit light. An organic light emitting display device includes pixels having organic light emitting diodes (OLEDs). An OED emits light of which a wavelength depends on an organic material included in the OLED. For example, the OLED includes organic material corresponding to one of a red color light, a green color light, and a blue color light. The organic light emitting display device displays the image by mixing the light emitted by the organic materials of the OLEDs.

Each of the pixels includes a plurality of transistors and a capacitor to drive the OLED therein, Depending, on the characteristics of the transistors, a leakage current may occur in some switching transistors. Accordingly, the display quality may be degraded.

SUMMARY

According to an exemplary embodiment of the inventive concept, an organic light emitting display device may include a plurality of pixels. Each of the plurality of pixels may include an organic light emitting diode (OLED), first to third transistors, a storage capacitor, and a first capacitor. The first transistor includes a gate electrode, a first electrode, and a second electrode. The second transistor includes a gate electrode receiving a first scan signal, a first electrode receiving a data signal, and a second electrode connected to the first electrode of the first transistor. The third transistor includes a gate electrode receiving a second scan signal, a first electrode connected to the second electrode of the first transistor, and a second electrode connected to the gate electrode of the first transistor. The storage capacitor includes a first electrode receiving a first power voltage and a second electrode connected to the gate electrode of the first transistor. The first capacitor includes a first electrode connected to the gate electrode of the third transistor and a second electrode receiving the first power voltage.

In exemplary embodiments of the inventive concept, the first transistor and the third transistor may be metal-oxide-semiconductor (MOS) transistors, and a channel type of the first transistor may be different from a channel, type of the third transistor.

In exemplary embodiments of the inventive concept, the second transistor and the third transistor may be MOS transistors, and a channel type of the second transistor may be different from a channel type of the third transistor. The second scan signal may be a signal that is the first scan signal inverted.

In exemplary embodiments of the inventive concept, each of the plurality of pixels may further include fourth to seventh transistors. The fourth transistor includes a gate electrode receiving a third scan signal, a first electrode receiving an initialization voltage, and a second electrode connected to, the gate electrode of the first transistor. The fifth transistor includes a gate electrode receiving an emission control signal, a first electrode receiving the first power voltage, and a second electrode connected to the first electrode of the first transistor. The sixth transistor includes a gate electrode receiving the emission control signal, a first electrode connected to the second electrode of the first transistor, and a second electrode connected to a first electrode of the OLED. The seventh transistor includes a gate electrode receiving a fourth scan signal, a first electrode receiving the initialization voltage, and a second electrode connected to the first electrode of the OLED.

In exemplary embodiments of the inventive concept, the first transistor, the fifth transistor, and the sixth transistor may be p-channel MOS transistors. The fourth transistor and the seventh transistor may be n-channel MOS transistors.

In exemplary embodiments of the inventive concept, the first transistor may be a p-channel MOS transistor. The second through seventh transistors may be n-channel MOS transistors.

In exemplary embodiments of the inventive concept, each of the Plurality of pixels may further include a second capacitor including a first electrode connected to the gate electrode of the first transistor and a second electrode connected to the gate electrode of the third transistor.

In exemplary embodiments of the inventive concept, a first capacitance of the first capacitor may be larger than a second capacitance of the second capacitor.

According to an exemplary embodiment of the inventive concept, an organic light emitting display device may include a base substrate, a first active pattern, a first gate insulating layer, a first gate pattern, a second gate insulating layer, a second gate pattern, a first insulating interlayer, a second active pattern, a third gate insulating layer, and a third gate pattern. The first active pattern is disposed on the based substrate, and includes an active region of a first transistor and an active region of a second transistor. The first gate insulating layer covers the first active pattern. The first gate pattern is disposed on the first gate insulating layer, and includes a gate electrode of the first transistor and a gate electrode of the second transistor. The second gate insulating layer covers the first gate pattern. The second gate pattern is disposed on the second gate insulating layer, and forms a storage capacitor with the first gate pattern. The first insulating interlayer covers the second gate pattern. The second active pattern is disposed on the first insulating interlayer, and includes an active region of a third transistor. The third gate insulating layer covers the second active pattern. The third gate pattern is disposed on the third gate insulating layer, includes a gate electrode of the third transistor, and forms a first capacitor with the second gate pattern.

In exemplary embodiments of the inventive concept, one of the first active pattern and the second active pattern may include an oxide semiconductor, and the other of the first active pattern and the second active pattern may include an inorganic semiconductor.

In exemplary embodiments of the inventive concept, the gate electrode of the second transistor may receive a first scan signal. The gate electrode of the third transistor may receive a second scan signal, and the second scan signal may correspond to a signal that is the first scan signal inverted.

In exemplary embodiments of the inventive concept, the second active pattern may further include an active region of a fourth transistor connected to the active region of the third transistor. The third gate pattern may further include a gate electrode of the fourth transistor receiving a third scan signal.

In exemplary embodiments of the inventive concept, the first active patter a may further include an active region of a fifth transistor and an active region of a sixth transistor that are connected to the active region of the first transistor. The first gate pattern may further include a gate electrode of the fifth transistor and a gate electrode of the sixth transistor that receive an emission control signal.

In exemplary embodiments of the inventive concept, the second active pattern may further include an active region of a seventh transistor connected to the active region of the fourth transistor. The third gate pattern may further include a gate electrode of the seventh transistor receiving a fourth scan signal.

In exemplary embodiments of the inventive concept, the organic light emitting display device may further include a second insulating interlayer covering the third gate pattern, and a source-drain pattern disposed on the second insulating interlayer.

In exemplary embodiments of the inventive concept, the second gate pattern may receive a first power voltage through the source-drain pattern.

In exemplary embodiments of the inventive concept, the first gate pattern may not overlap the third gate pattern in a region in which the first capacitor is formed.

According to an exemplary embodiment of the inventive concept, a pixel may include an organic light emitting diode ((RED), first to third transistors, a storage capacitor, and a first capacitor. The first transistor includes a gate electrode, a first electrode, and a second electrode. The second transistor includes a gate electrode receiving a first scan signal a first electrode receiving a data signal, and a second electrode connected to the first electrode of the first transistor. The third transistor includes a gate electrode receiving a second scan signal, a first electrode connected to the second electrode of the first transistor, and a second electrode connected to the gate electrode of the first transistor. The storage capacitor includes a first electrode receiving a first power voltage and a second electrode connected to the gate electrode of the first transistor. The first capacitor includes a first electrode connected to the gate electrode of the third transistor and a second electrode receiving the first power voltage.

In exemplary embodiments of the inventive concept, the first transistor and the third transistor may be metal-oxide-semiconductor (MOS) transistors, and a channel type of the first transistor may be different from a channel type of the third transistor.

In exemplary embodiments of the inventive concept, the second transistor and the third transistor may be MOS transistors, and a channel type of the second transistor may be different from a channel type of the third transistor. The second scan signal may be a signal that is the first scan signal inverted.

BRIEF DESCRIPTION OF THE DRAWINGS

The above and other features of the inventive concept will be more clearly understood by describing in detail exemplary embodiments thereof with reference to the accompanying drawings.

DETAILED DESCRIPTION OF THE EMBODIMENTS

Figure 1:
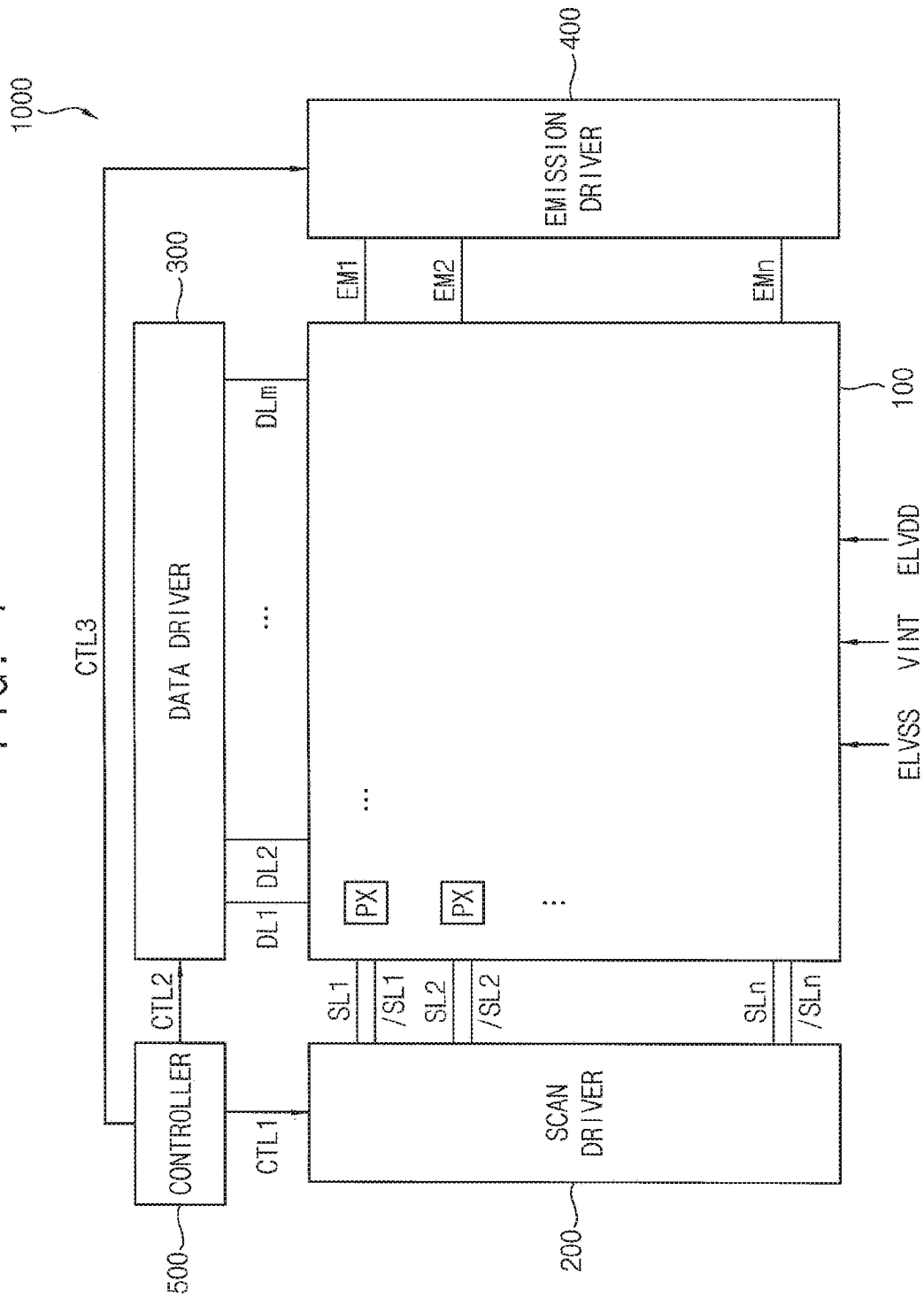
FIG. 1 is a block diagram illustrating an organic light emitting display device according to an exemplary embodiment of the inventive concept.

Exemplary embodiments of the inventive concept provide an organic light emitting display device with increased display quality.

Exemplary embodiments of the inventive concept also provide a pixel for the organic light emitting display device.

Exemplary embodiments of the inventive concept will be described more fully hereinafter with reference to the accompanying drawings. Like reference numerals may refer to like elements throughout this application.

FIG. 1 is a block diagram illustrating an organic light emitting display (OLED) device according to an exemplary embodiment of the inventive concept.

Referring to FIG. 1, an organic light emitting display device 1000 may include a display panel 100, a scan driver 200, a data driver 300, an emission control driver 400, and a controller 500.

The display panel 100 may include a plurality of pixels PX to display an image. For example, the display panel 100 may include n*m pixels PX because the pixels PX are arranged at locations corresponding to crossing points of scan lines SL1 through Sim and data lines DL through DLm, where, n and m are integers greater than 1. Each of the pixels PX may include a driving transistor and a plurality of switching transistors. In an exemplary embodiment of the inventive concept, the driving transistor may be a p-channel MOS transistor, and some switching transistors that are located in positions in which a leakage current easily occurs may be n-channel MOS transistors. Therefore, the pixels PX may be formed using first and second active patterns and first through third gate patterns. For example, the p-channel MOS transistors may be formed using the first active pattern and the first gate pattern. The n-channel MOS transistors may be firmed using the second active pattern and the third gate pattern. In addition, each of the pixels PX may include a first capacitor formed by overlapping the second gate pattern and the third gate pattern to reduce a kickback effect. The structure of each of the pixels PX will be described in detail with reference to FIGS. 2 and 5A through 5F.

The scan driver 200 may progressively provide a first scan signal to the pixels PX via the scan lines SL1 through SLn based on a first control signal CTL1. The scan driver 200 may also progressively provide a second scan signal to the pixels PX via inverted scan lines /SL1 through /SLn based on the first control signal CTL1. For example, the second scan signal may correspond to an inversion of the first scan signal (e.g., the first scan signal inverted).

The data driver 300 may provide a data signal to the pixels PX via the data lines DL1 through DLm based on a second control signal CTL2.

The emission control driver 400 may provide an emission control signal to the pixels PX via emission control lines EM1 through EMn based on a third control signal CTL3.

The controller 500 may control the scan driver 200, the data driver 300, and the emission control driver 400. The controller 500 may generate the first through third control signals CTL1, CTL2, and CTL3 to control the scan driver 200, the data driver 300, and the emission control driver 400, respectively. The first control signal CTL1 for controlling the scan driver 200 may include a vertical start signal, scan clock signals, etc. The second control signal CTL2 for the controlling the data driver 300 may include digital image data, a horizontal start signal, etc. The third control signal CTL3 for the controlling the emission control driver 400 may include an emission control start signal, emission control clock signals, etc.

Further, the organic light emitting display device 1000 may further include a power supply providing a first power voltage ELVDD, a second power voltage ELVSS, and an initialization voltage VINT to the display panel 100.

Figure 2:
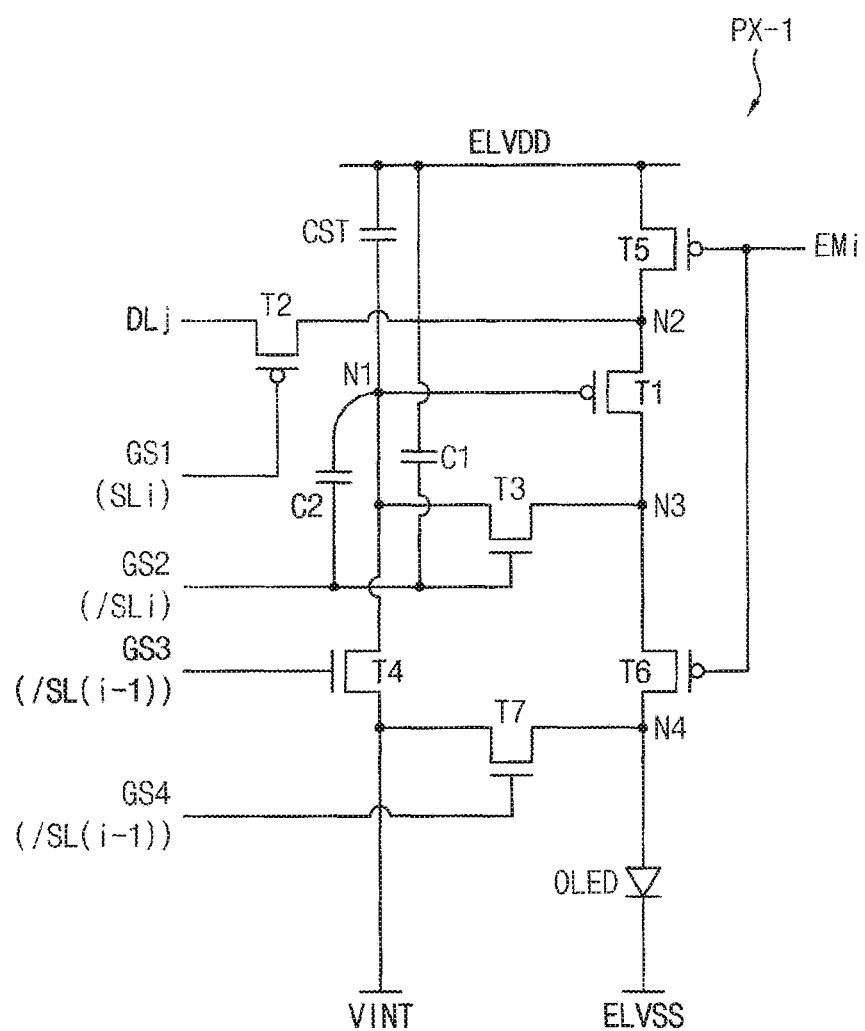
FIG. 2 is a diagram illustrating a pixel included in the organic light emitting display device of FIG. 1 according to an exemplary embodiment of the inventive concept.

FIG. 2 is a diagram illustrating a pixel included in the organic light emitting display device of FIG. 1 according to an exemplary embodiment of the inventive concept.

Referring to FIG. 1, a pixel PX-1 may include first through seventh transistors T1 through T7, a storage capacitor CST, a first capacitor C1, and an OLED. The pixel PX-1 may be located at an (i)th pixel row and a (j)th pixel column, where i is an integer between 1 and n, and j is an integer between 1 and m.

The first transistor T1 may be a driving transistor providing a driving current corresponding to a data signal to the OLED. The first transistor T1 may include a gate electrode connected to a first node N1, a first electrode connected to a second node N2, and a second electrode connected to a third node N3.

The second transistor T2 may provide a data signal to the first transistor T1 in response to a first scan signal GS1 applied to an (i)th scan line SLi. In an exemplary embodiment of the inventive concept, the second transistor T2 may include a gate electrode receiving the first scan signal GS1 from the (i)th scan line SLi, a first electrode receiving the data signal from a (j)th data line DLj, and a second electrode connected to the first electrode of the first transistor T1 (e.g., the second node N2).

The third transistor T3 may connect the second electrode of the first transistor T1 to the gate electrode of the first transistor T1 in response to a second scan signal GS2 applied to an (i)th inverted scan line /SLi. In an exemplary embodiment of the inventive concept, the third transistor T3 may include a gate electrode receiving the second scan signal GS2 from the (i)th inverted scan line /SLi, a first electrode connected to the second electrode of the first transistor T1 (e.g., the third node N3), and a second electrode connected to the gate electrode of the first transistor T1 (e.g., the first node N1).

The fourth transistor T4 may apply the initialization voltage VINT to the gate electrode of the first transistor T1 in response to a third scan signal GS3 applied to an (i−1)th inverted scan line /SL(i−1). In an exemplary embodiment of the inventive concept, the fourth transistor T4 may include a gate electrode receiving the third scan signal GS3 from the (i−1)th inverted scan line /SL(i−1), a first electrode receiving the initialization voltage VINT, and a second electrode connected to the gate electrode of the first electrode T1 (e.g., the first node N1).

The fifth transistor T5 may apply the first power voltage ELVDD to the first electrode of the first transistor T1 in response to an emission control signal. In an exemplary embodiment of the inventive concept, the fifth transistor T5 may include a gate electrode receiving the emission control signal front an (i)th emission control line a first electrode receiving the first power voltage ELVDD, and a second electrode connected to the first electrode of the first transistor T1 (e.g., the second node N2).

The sixth transistor T6 may connect the second electrode of the first transistor T1 to the first electrode of the OLED in response to the emission control signal. In an exemplary embodiment of the inventive concept, the sixth transistor T6 may include, a gate electrode receiving the emission control signal from the (i)th emission control line EMi a first electrode connected to the second electrode of the first transistor T1 (e.g., the third node N3), and a second electrode connected to the first electrode of the OLED (e.g., a fourth node N4).

The seventh transistor T7 may apply the initialization voltage VINT to the first electrode of the OLED in response to a fourth scan signal GS4 applied to an (i−1)th inverted scan line /SL(i−1). In an exemplary embodiment of the inventive concept, the seventh transistor T7 may include a gate electrode receiving the fourth scan signal GS4 from the (i−1)th inverted scan line /SL(i−1), a first electrode receiving the initialization voltage VINT, and a second electrode connected to the first electrode of the OLED (e.g., the fourth node N4). Here, the fourth scan signal GS4 and the third scan signal GS3 are both from the (i−1)th inverted scan line /SL(i−1), and thus may be the same signal.

The storage capacitor CST may include a first electrode receiving the first power voltage. ELVDD and a second electrode connected to the gate electrode of the first transistor T1 (e.g., the first node N1). In an exemplary embodiment of the inventive concept, the storage capacitor CST may be formed using a first gate pattern including the gate electrode of the first transistor T1 and a second gate pattern receiving the first power voltage ELVDD.

The first capacitor C1 may include a first electrode connected to the gate electrode of the third transistor T3 and a second electrode receiving the first power voltage ELVDD. In an exemplary embodiment of the inventive concept, the first capacitor C1 may be formed using the second gate pattern receiving the first power voltage ELVDD and a third gate pattern including the gate electrode of the third transistor T3.

In an exemplary embodiment of the inventive concept, the pixel PX-1 may further include a second capacitor C2. For example, the second capacitor C2 may be a parasitic capacitor. The second capacitor C2 may include a first electrode connected to the gate electrode of the first transistor T1 and a second electrode connected to the gate electrode of the third transistor T3.

In an exemplary embodiment of the inventive concept, the first transistor T1, the second transistor T2, the fifth transistor T5, and the sixth transistor T6 may be p-channel MOS transistors. On the other hand, the third transistor T3, the fourth transistor T4, and the seventh transistor T7 may be n-channel MOS transistors. In other words, the driving transistor and some switching transistors located in positions in which leakage current does not occur may be implemented as p-channel MOS transistors to, enhance reliability. Display quality degradation due to the leakage current may be easily recognized when the display panel is driven at a low frequency. Therefore, the other switching transistors located in positions in which the leakage current easily occurs may be implemented as n-channel MOS transistors. Accordingly, the second scan signal GS2 may correspond to an inversion of the first scan signal GS1.

Although FIG. 2 shows the gate electrode of the fourth transistor T4 and the gate electrode of the seventh transistor T7 receiving the inverted scan signal (e.g., GS3/GS4) from the (i−1)th inverted scan line /SL(i−1), the inventive concept is not limited thereto. For example, the fourth transistor T4 and the seventh transistor T7 may be connected to different scan lines. In this case, the scan driver may include a plurality of stages for outputting the first scan signal GS1, the second scan signal GS2, the third scan signal GS3, and the fourth scan signal GS4 as scan signals.

Although FIG. 2 shows that the pixel PX-1 includes the first to seventh transistors T1 to T7, the pixel PX-1 may have a variety of structures.

Figure 3:
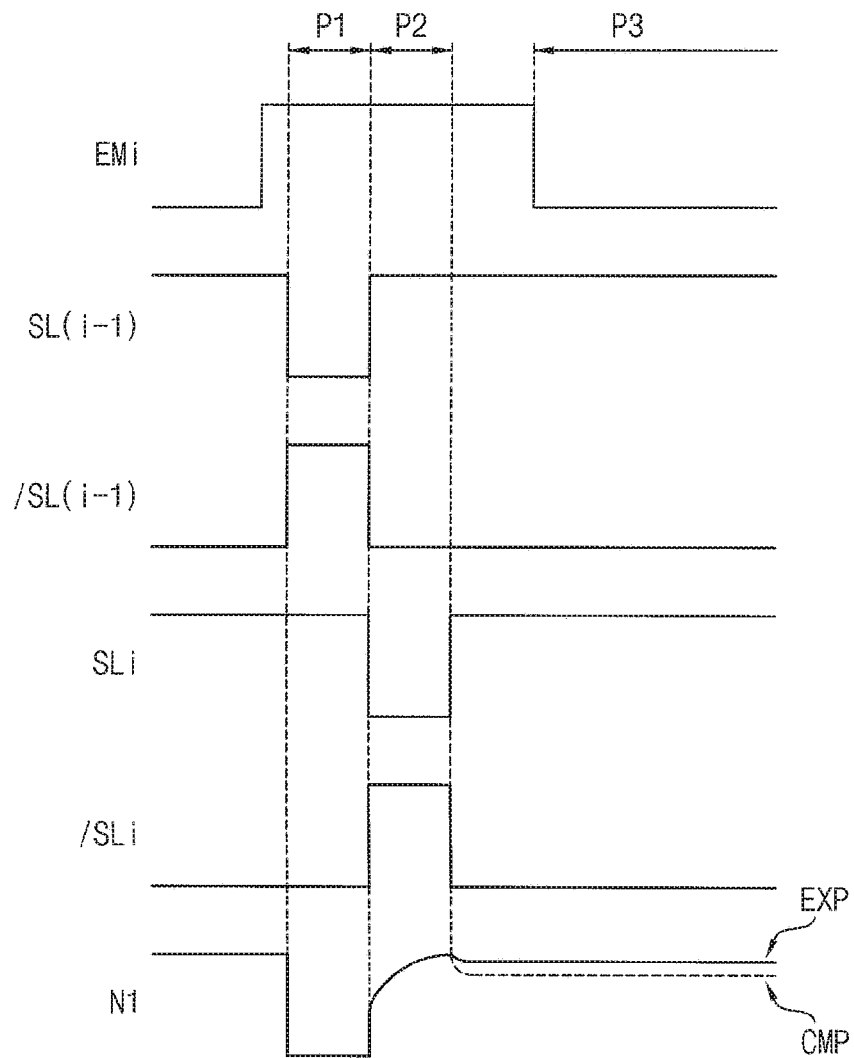
FIGS. 3 and 4 are diagrams for describing an effect of decreasing a kickback effect by a first capacitor included in the pixel of FIG. 2 according to an exemplary embodiment of the inventive concept.
Figure 4:
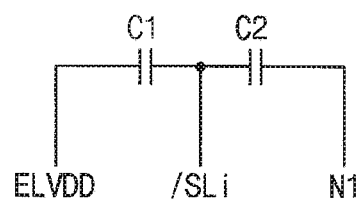

FIGS. 3 and 4 are diagrams for describing an elect of decreasing a kickback effect by a first capacitor included in the pixel of FIG. 2 according to an exemplary embodiment of the inventive concept.

Referring to FIGS. 2, 3, and 4, in the pixel PX-1, a kickback phenomenon may occur due to the second capacitor C2 (e.g., a parasitic capacitor) between a wiring connected to the gate electrode of the third transistor T3 and a wiring connected to the gate electrode of the first transistor T1. In particular, when the first transistor T1 and the third transistor T3 are MOS transistors of different types, a voltage of the gate electrode of the first transistor T1 (e.g., the first node N1) may be decreased by a switching operation of the third transistor T3 (e.g., the kickback phenomenon). Therefore, the pixel PX-1 may include the first capacitor C1 located between the gate electrode of the third transistor T3 and the first power voltage ELVDD to reduce influence from the kickback phenomenon.

For example, as shown in FIG. 3, in the pixel PX-1 located at the (i)th pixel row, the fourth transistor T4 and the seventh transistor T7 may be turned on in response to the inverted scan signal from the (i−1)th inverted scan line /SL(i−1) during, an initialization period P1. Accordingly, the initialization voltage VINT may be applied to the gate electrode of the first transistor T1 (e.g., the first node N1) and the OLED. During a data programming and threshold voltage compensation period P2, the second transistor T2 may be turned on in response to the scan signal from the (i)th scan line SLi, and the third transistor T3 may be turned on in response to the inverted scan signal from the (i)th inverted scan line /SLi. Accordingly, the voltage of the first node N1 may be set to a voltage to which a threshold voltage of the first transistor T1 is compensated for the data signal. During an emission period P3, the fifth transistor T5 and the sixth transistor T6 may be turned on in response to an emission control signal from the (i)th emission control line EMi. Therefore, the driving current corresponding to the data signal may flow to the OLED.

As a comparison, assuming the pixel PX-1 does not include the first capacitor C1, a voltage (CMP) of the first node N1 experiences a relatively large decrease due to the second capacitor C2 between the gate electrode of the third transistor T3 and the first node N1, when the voltage of the gate electrode of the third transistor T3 is changed immediately after the data programming and threshold voltage compensation period P2. For example, the voltage of the first node N1 may decrease from 2.75V to 2.32V. Thus, a voltage margin for a black color data may decrease, and a voltage for the black color data may increase.

On the other hand, in exemplary embodiments of the inventive concept, where the pixel PX-1 includes the first capacitor C1, a voltage (EXP) of the first node N1 has a relatively small decrease because the kickback effect is reduced by the first capacitor C1. For example, the voltage of the first node N1 may decrease from 2.75V to 2.69V. As shown in FIG. 4, the first capacitor C1 may be located between the first power voltage ELVDD and the gate electrode of the third transistor T3 (or the (i)th inverted scan line /SLi). The second capacitor C2 may be located between the gate electrode of the third transistor T3 (or the (i)th inverted scan line /SLi) and the gate electrode of the first transistor T1 (or the first node N1). Accordingly, a change amount of the voltage of the gate electrode of the first transistor T1 due to the kickback phenomenon may be calculated according to [Equation 1].

$$\Delta V_{T1g} = \frac{C2}{C1 + C2 + Ct} \times \Delta V_{T3g}, \quad [\text{Equation 1}]$$

$\Delta V_{T1g}$ indicates a change amount of the voltage of the gate electrode of the first transistor T1, C1 indicates a capacitance of the first capacitor C1, C2 indicates a capacitance of the second capacitor C2, Ct indicates total capacitances of other parasitic capacitors affecting the gate electrode of the first transistor T1, and $\Delta V_{T3g}$ indicates a change amount of the voltage of the gate electrode of the third transistor T3.

Therefore, the change amount due to the kickback phenomenon decreases as the capacitance of the first capacitor C1 increases. Accordingly, in an exemplary embodiment of the inventive concept, a first capacitance of the first capacitor C1 may be larger than a second capacitance of the second capacitor C2, to reduce the effect of the kickback phenomenon.

FIGS. 5A through 5F are diagrams illustrating an example of forming the pixel of FIG. 2 according to an exemplary embodiment of the inventive concept. FIG. 6 is a cross-sectional view taken along line I1-I2 of FIG. 5F according to an exemplary embodiment of the inventive concept. FIG. 7 is a cross-sectional view taken along line I3-I4 of FIG. 5F according to an exemplary embodiment of the inventive concept.

Referring to FIGS. 5A through 5F, 6, and 7, the first, second, fifth, and sixth transistors T1, T2, T5, and T6 may be formed using a first active pattern 120 and first gate patterns 130A, 130B, and 130C, The storage capacitor CST may be formed using the first gate pattern 130B and a second gate pattern 140A. The third, fourth, and seventh transistors T3, T4, and T7 may be formed using a second active pattern 150 and third gate patterns 160A and 160B. Additionally, the first capacitor C1 may be formed using the second gate pattern 140A and the third gate pattern 160A.

As shown in FIG. 6, a buffer layer 115 may be disposed on a base substrate 110. The base substrate 110 may include a transparent insulation substrate. For example, the base substrate 110 may include a glass substrate, a quartz substrate, a transparent resin substrate, etc. The buffer layer 115 may prevent diffusion of metal atoms and/or impurities from the base substrate 110. Additionally, the buffer layer 115 may adjust a heat transfer rate of a successive crystallization process for the first active pattern 120, to obtain uniformity in the first active pattern 120. The buffer layer 115 may be formed using a silicon compound.

Figure 5A:
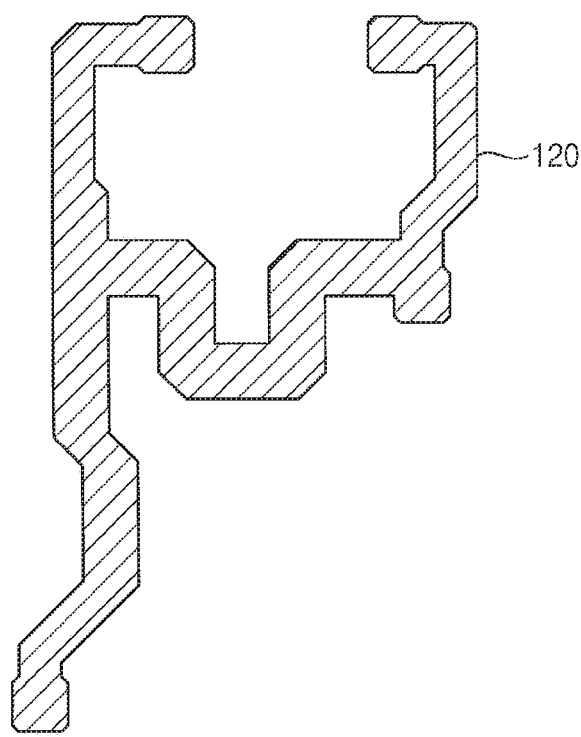
FIGS. 5A through 5F are diagrams illustrating an example of forming the pixel of FIG. 2 according to an exemplary embodiment of the inventive concept.
Figure 6:
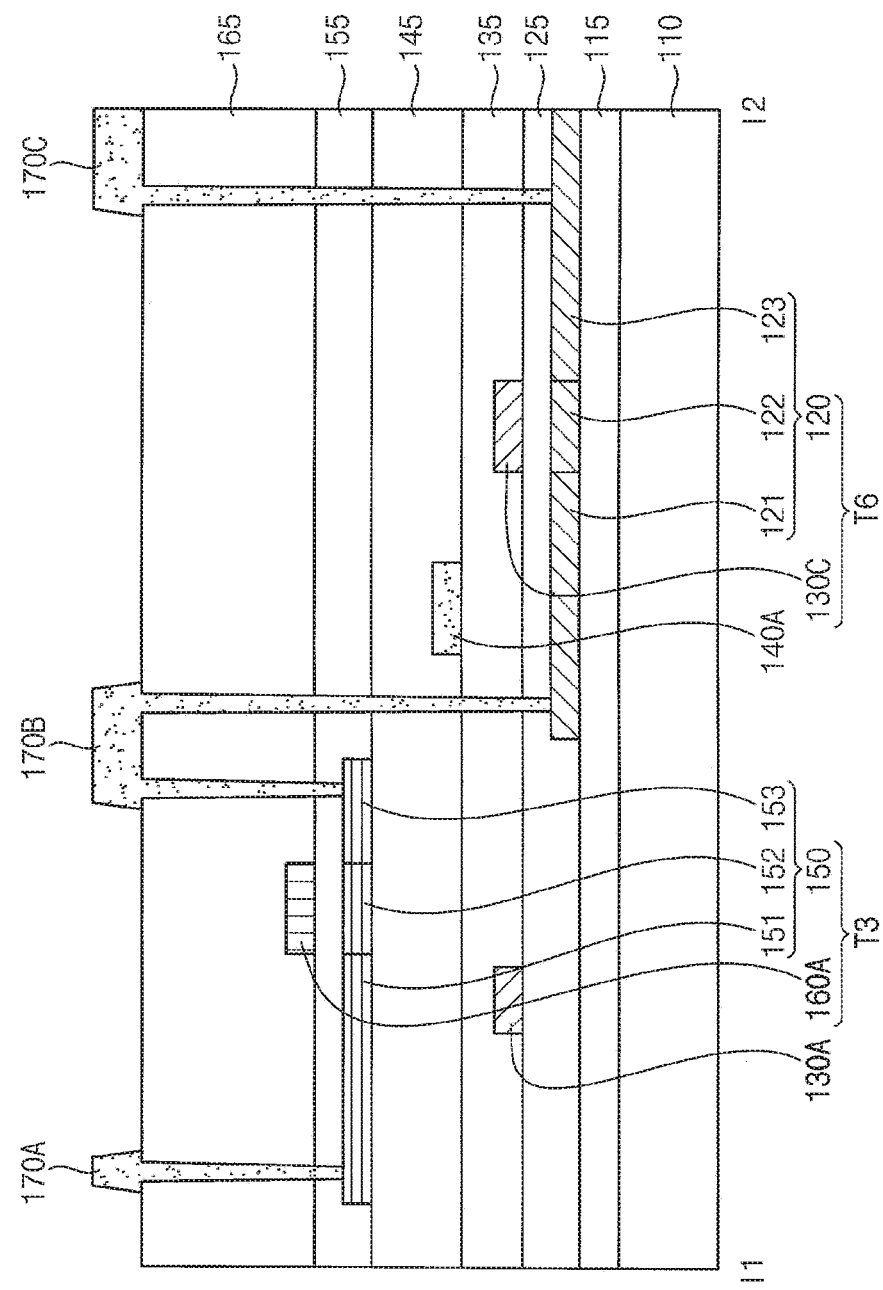
FIG. 6 is a cross-sectional view taken along I1-I2 of FIG. 5F according to an exemplary embodiment of the inventive concept.
Figure 7:
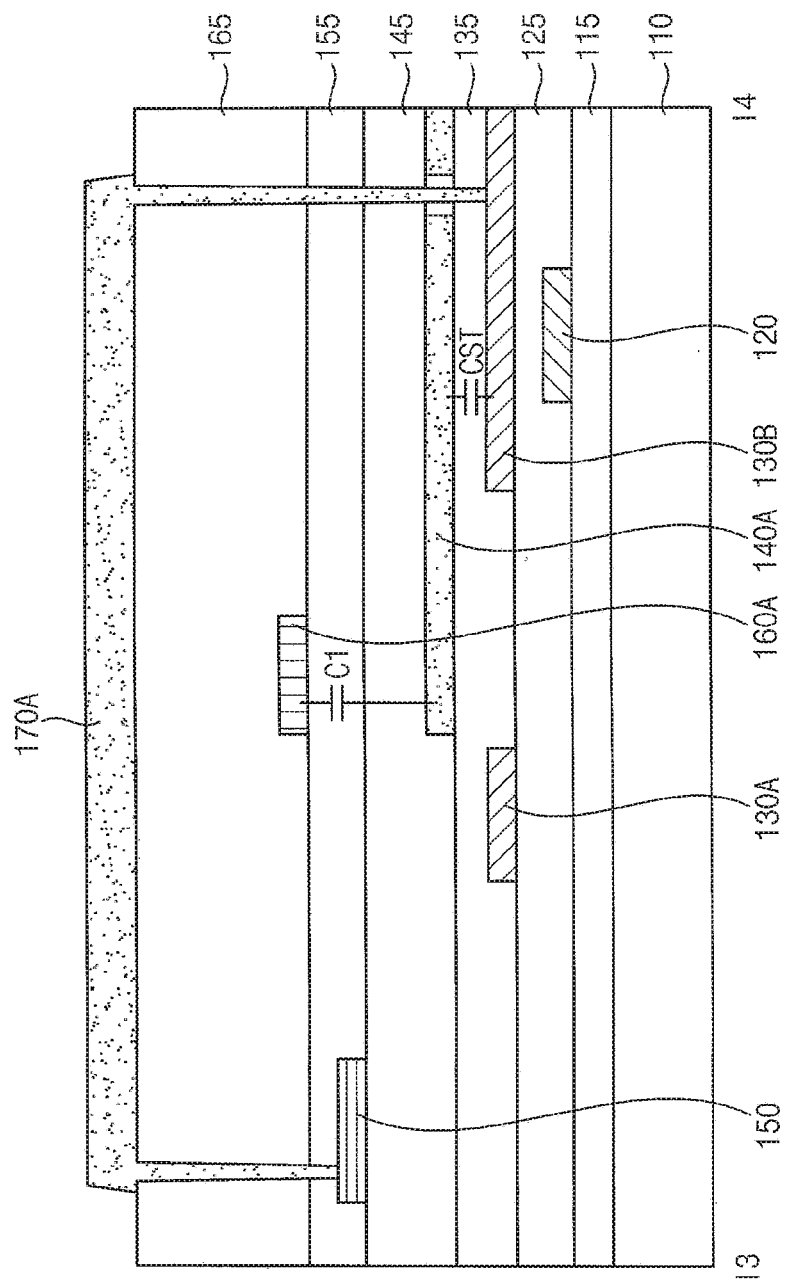
FIG. 7 is a cross-sectional view taken along line I3-I4 of FIG. 5F according to an exemplary embodiment of the inventive concept.

As shown in FIGS. 5A and 6, the first active pattern 120 may be disposed on the buffer layer 115. A semiconductor layer may be formed on the buffer layer 115, and then a preliminary active layer may be formed on the buffer layer 115 by patterning the semiconductor layer. The crystallization process may be performed on the preliminary active layer to form the first active pattern 120 on the buffer layer 115.

Figure 5B:
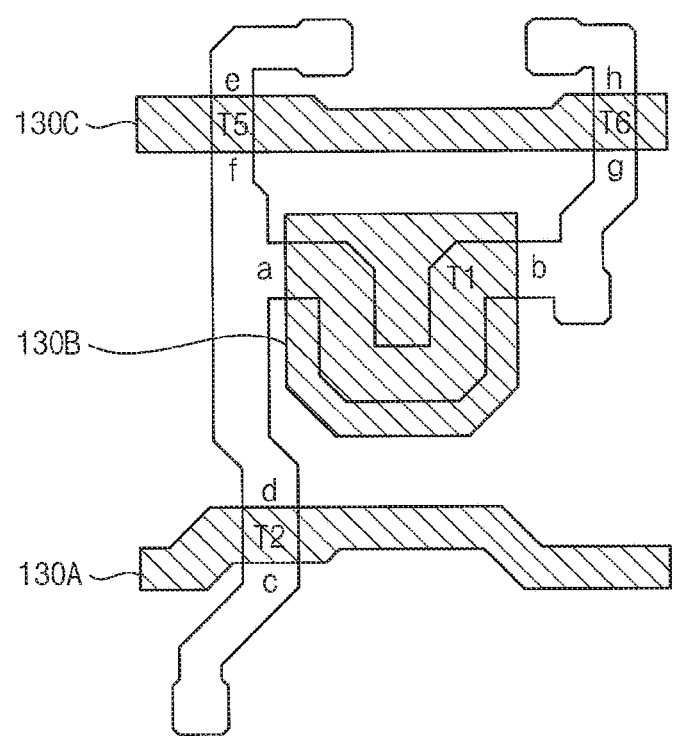

As shown in FIGS. 5A, 5B, and 6, the first active pattern 120 may include active regions of the first, second, fifth, and sixth transistors T1, T2, T5, and T6. The first active pattern 120 may include first through eighth regions a, b, c, d, e, f, g, and h. The first through eighth regions a, b, c, d, e, f, g, and h may be doped by an impurity such that the first through eighth regions a, b, c, d, e, f, g, and h may have a higher electrical conductivity than other region of the first active pattern 120. The first through eighth regions a, b, c, d, e, f, g, and h may be used to form source or drain electrodes of the first, second, fifth, and sixth transistors T1, T2, T5, and T6. Boundaries of the first through eighth regions a, b, c, d, e, f, g, and h may not be clearly divided and may be electrically connected to one another. For example, the first region a may not be clearly divided from the fourth region d and sixth region f, and may be electrically connected to one another.

A first gate insulating layer 125 may cover the first active pattern 120, and may be disposed on the buffer layer 115. In an exemplary embodiment of the inventive concept, the first gate insulating layer 125 may sufficiently cover the first active pattern 120, and may have a substantially level surface without a step around the first active pattern 120. In other words, the first gate insulating layer 125 may be disposed over and cover both the buffer layer 115 and the first active pattern 120, and an upper surface of the first gate insulating layer may be substantially level. In an exemplary embodiment of the inventive concept, the first gate insulating layer 125 may cover the first active pattern 120 on the buffer layer 115, and may be disposed with a substantially uniform thickness along a profile of the first active pattern 120 or the buffer layer 115 where the first active pattern 120 is not disposed.

As shown in FIGS. 6 and 7, the first gate patterns 130A, 130B, and 130C may be disposed on the first gate insulating layer 125. For example, the first gate patterns 130A, 130B, and 130C may include a scan line 130A to which the first scan signal GS1 is applied, a gate electrode 130B of the first transistor T1, and an emission control line 130C to which the emission control signal is applied. The first active pattern 120 and the first gate patterns 130A, 130B, and 130C may be arranged to form the first, second, fifth, and sixth transistors T1, T2, T5, and T6. Thus, the first gate patterns 130A, 130B, and 130C may be positioned on a portion of the first gate insulating layer 125 under which the first active pattern 120 is located. The first gate patterns 130A, 130B, and 130C may include a metal, an alloy, a conductive metal oxide, a transparent conductive material, etc.

A second gate insulating layer 135 may cover the first gate patterns 130A, 130B, and 130C, and may be disposed on the first gate insulating layer 125. In one example, the second gate insulating layer 135 may sufficiently cover the first gate patterns 130A, 130B, and 130C, and may have a substantially level surface without a step around the first gate patterns 130A, 130B, and 130C. In another example, the second gate insulating layer 135 may cover the first gate patterns 130A, 130B, and 130C on the first gate insulating layer 125 and may be disposed, with a substantially uniform thickness along a profile of the first gate patterns 130A, 130B, and 130C.

Figure 5C:
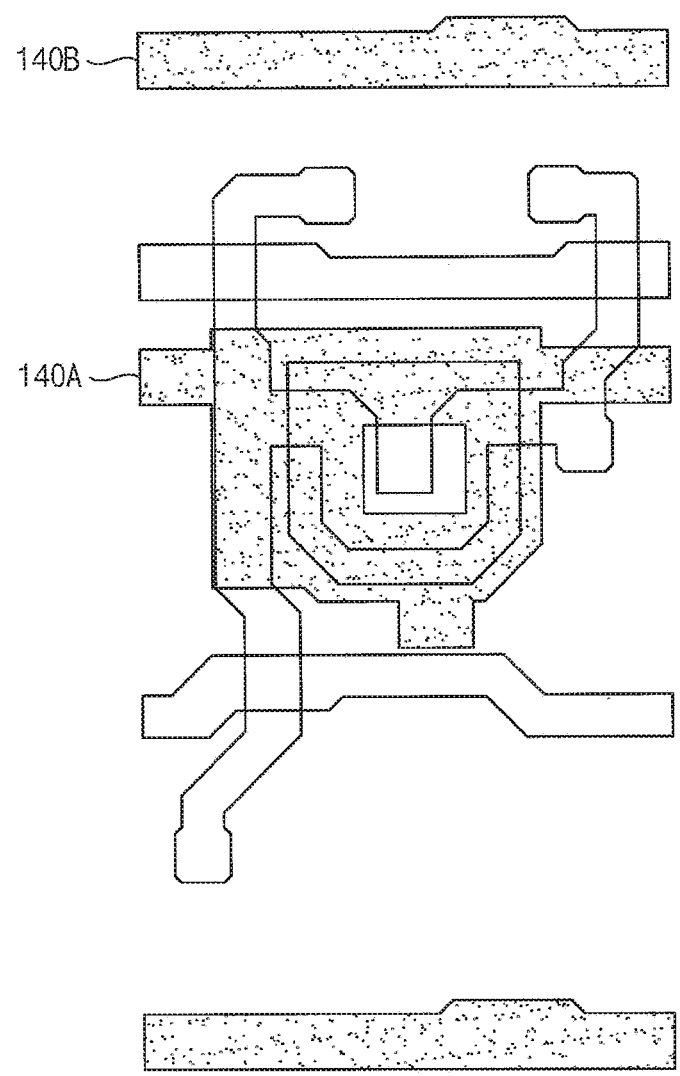

As shown in FIGS. 5C and 6, the second gate pattern 140A and a second gate pattern 140B may be disposed on the second gate insulating layer 135. For example, the second gate patterns 140A and 140B may include a second electrode 140A of the first capacitor C1 to which the first power voltage ELVDD is applied and an initialization voltage line 140B to which the initialization voltage VINT is applied. The gate electrode 130B of the first transistor T1 and the second electrode 140A of the first capacitor C1 may form the storage capacitor CST. The second gate patterns 140A and 140B may include a metal, an alloy, a conductive metal oxide, a transparent conductive material, etc.

A first insulating interlayer 145 may cover the second gate patterns 140A and 140B and may be disposed on the second gate insulating layer 135. In one example, the first insulating interlayer 145 may sufficiently cover the second gate patterns 140A and 140B on the second gate insulating layer 135, and may have a substantially level surface without a step around the second gate patterns 140A and 140B. In another example, the first insulating interlayer 145 may cover the second gate patterns 140A and 140B on the second gate insulating layer 135, and may be disposed with a substantially uniform thickness along a profile of the second gate patterns 140A and 140B.

Figure 5D:
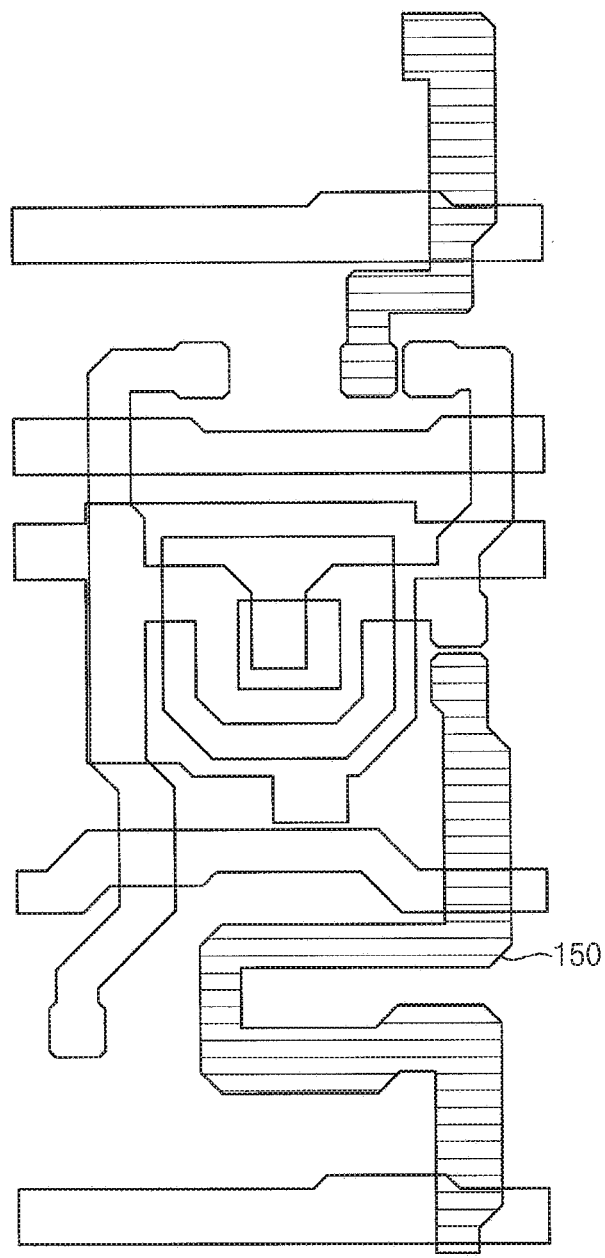

As shown in FIGS. 5D and 6, the second active pattern 150 may be disposed on the first insulating interlayer 145. A semiconductor layer may be formed on the first insulating interlayer 145, and then a preliminary active layer may be formed on the first insulating interlayer 145 by patterning the semiconductor layer. The crystallization process may be performed on the preliminary active layer to form the second active pattern 150 on the first insulating interlayer 145.

Figure 5E:
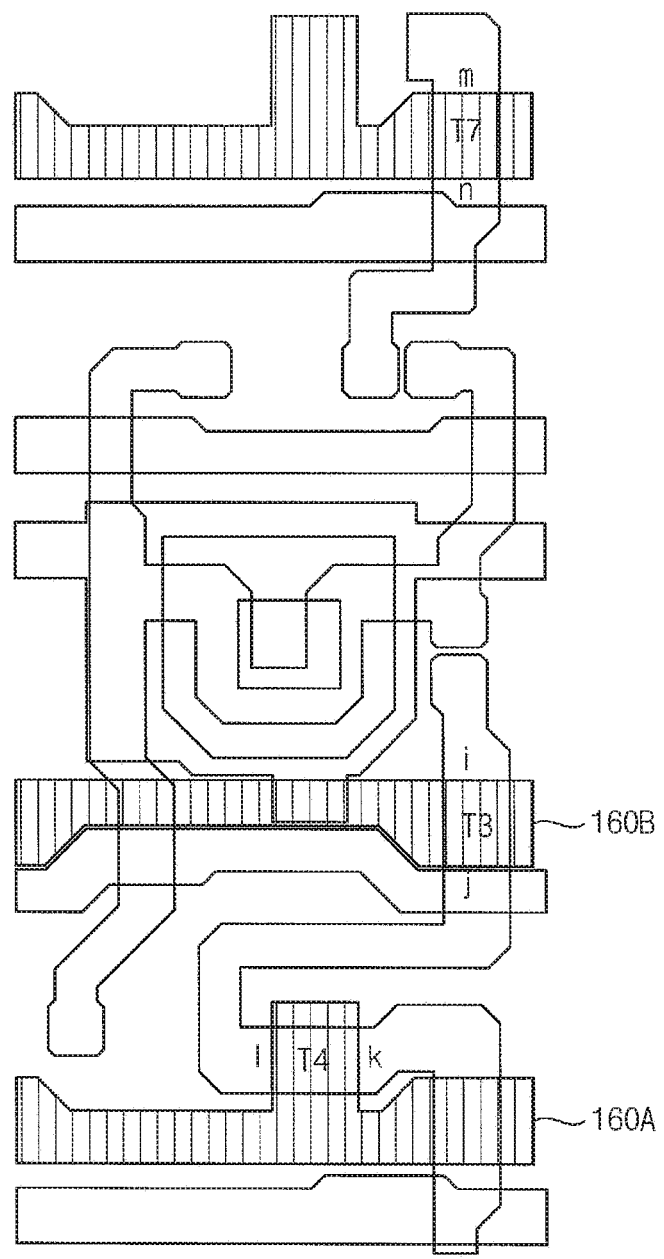

As shown in FIG. 5E, the second active pattern 150 may include active regions of the third, fourth, and seventh transistors T3, T4, and T7. The second active pattern 150 may include ninth through fourteenth regions i, j, k, l, m, and n. The ninth through fourteenth regions i, j, k, l, m, and a may be doped by an impurity such that the ninth through fourteenth regions i, j, k, l, m, and n may have a higher electrical conductivity than other regions of the second active pattern 150. The ninth through fourteenth regions i, j, k, l, m, and n may be used to form source or drain electrodes of the third, fourth, and seventh transistors T3, T4, and T7. Boundaries of the ninth through fourteenth regions i, j, k, l, m, and n may not be clearly divided and may be electrically connected to one another.

A third gate insulating layer 155 may cover the second active pattern 150, and may be disposed on the first insulating interlayer 145. In one example, the third gate insulating layer 155 may sufficiently cover the second active pattern 150, and may have a substantially level surface without a step around the second active pattern 150. In another example, the third, gate insulating layer 155 may cover the second active pattern 150 on the first insulating interlayer 145, and may be disposed with a substantially uniform thickness along a profile of the second active pattern 150.

The third gate patterns 160A and 160B may be disposed on the third gate insulating layer 155. For example, the third gate patterns 160A and 160B may include a scant line 160A to which the second scan signal GS2 (e.g., an inverted scan signal of a current pixel row) is applied and a scan line 160B to which the third or fourth scan signals GS3 or GS4 (e.g., an inverted scan signal of a previous pixel row) is applied. The second active pattern 150 and the third gate patterns 160A and 160B may be arranged to form the third, fourth, and seventh transistors T3, T4, and T7. Thus, the third gate patterns 160A and 160B may be positioned on a portion of the third gate insulating layer 155 under which the second active pattern 150 is located.

A second insulating interlayer 165 may cover the third gate patterns 160A and 160B and may be disposed on the third gate insulating layer 155. In one example, the second insulating interlayer 165 may sufficiently cover the third gate patterns 160A and 160B on the third gate insulating layer 155, and may have a substantially level surface without a step around the third gate patterns 160A and 160B. In another example, the second insulating interlayer 165 may cover the third gate patterns 160A and 160B on the third gate insulating layer 155, and may be disposed with a substantially uniform thickness along a profile of the third gate patterns 160A and 160B.

Figure 5F:
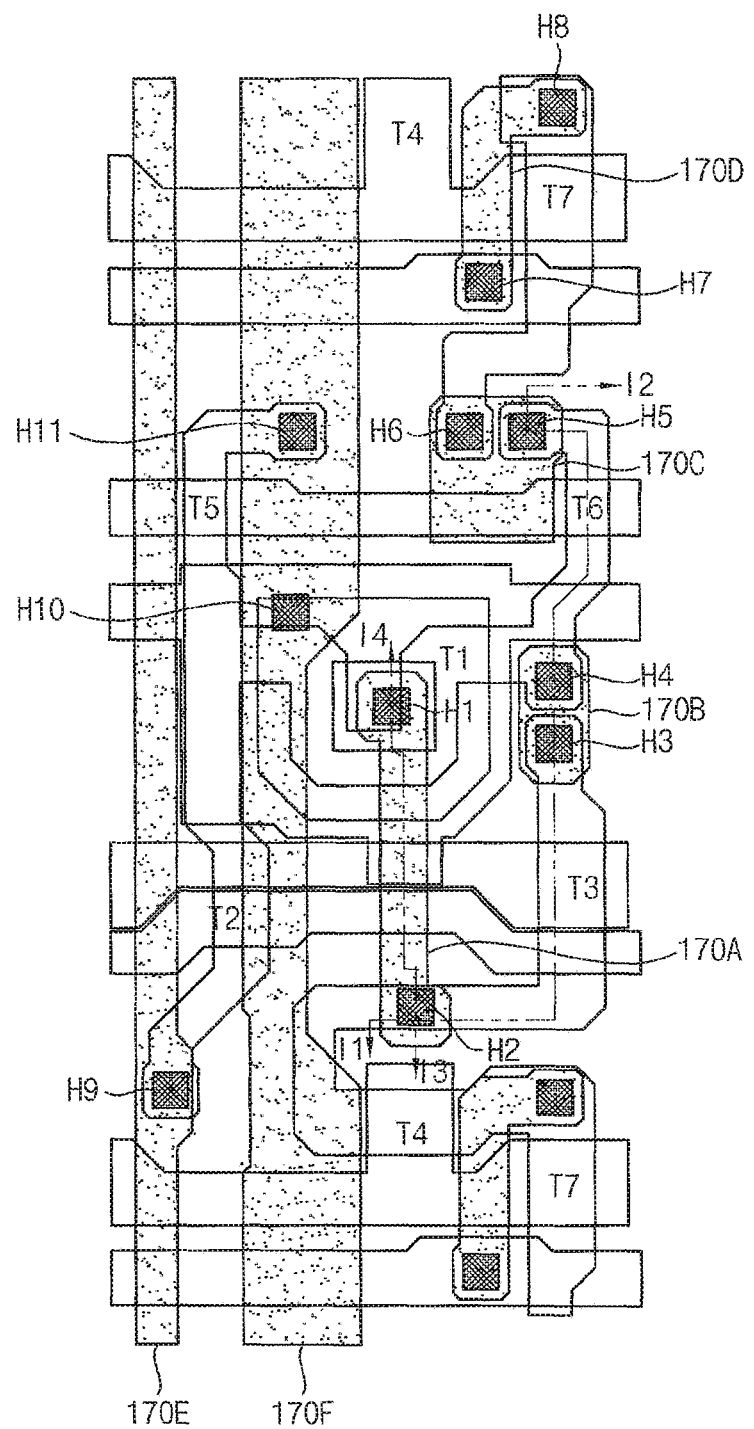

As shown in FIG. 5F, first through eleventh contact holes H1 through H11, which expose at least one of the first active pattern 120, the first gate pattern 130B, the second gate patterns 140A and 140B, and the second active pattern 150, may be formed by partially patterning the insulating layers. Thereafter, source-drain patterns 170A, 170B, 170C, 170D, 170E, and 170F may be formed on the second insulating interlayer 165 by filling the first through eleventh contact holes H1 through H11.

The source-drain patterns 170A through 170E may include a first connecting portion 170A, a second connecting portion 170B, a third connecting portion 170C, a fourth connecting portion 170D, a data line 170E, and a power voltage line 170F. The first connecting portion 170A may be electrically connected to the gate electrode 130B of the first transistor T1 through the first contact hole H1 and may be electrically connected to the second active pattern 150 (e.g., between the third and fourth transistors T3 and T4) through the second contact hole H2. The second connecting portion 170B may be electrically connected to the second active pattern 150 (e.g., the active region of the third transistor T3) through the third contact hole H3, and may be electrically connected to the first active pattern 120 (e.g., an active region of the first transistor T1) through the fourth contact hole H4. The third connecting portion 170C may be electrically connected to the first active pattern 120 (e.g., an active region of the sixth transistor T6) through the fifth contact hole H5, and may be electrically connected to the second active pattern 150 (e.g., an active region of the seventh transistor T7) through the sixth contact hole H6. The fourth connecting portion 170D may be electrically connected to the initialization voltage line 140B through the seventh contact hole H7 and may be electrically connected to the second active pattern 150 (e.g., an active region of the seventh transistor T7) through, the eighth contact hole H8. The data line 170E may receive the data signal and may be electrically connected to the first active pattern 120 (e.g., an active region of the second transistor T2) through the ninth contact hole H9. The power voltage line 170F may receive the first power voltage ELVDD, may be electrically connected to the second gate pattern (e.g., the second electrode 140A of the first, capacitor C1) through the tenth contact hole H10, and may be electrically connected to the first active pattern 120 (e.g., an active region of the fifth transistor T5) through the eleventh contact hole H11.

As shown in FIG. 6, the first, second, fifth, and sixth transistors T1, T2, T5, and T6 may be formed using the first active pattern 120 and the first gate patterns 130A, 130B, and 130C. For example, an active region 122 of the sixth transistor T6 and regions 121 and 123 for forming the source or the drain electrode of the sixth transistor T6 may be formed with the first active pattern 120. In addition, the gate electrode of the sixth transistor T6 may be formed with the first gate pattern 130C. The source-drain patterns 170B and 170C may be electrically connected to the regions 121 and 123 fix forming the source or the drain electrode of the sixth transistor T6 through the fourth and fifth contact holes H4 and H5.

The third, fourth, and seventh transistors T3, T4, and T7 may be formed using the second active pattern 150 and the third gate patterns 160A, 160B, and 160C. For example, an active region 152 of the third transistor T3 and regions 151 and 153 for forming the source or drain electrode of the third transistor T3 may be formed with the second active pattern 150. In addition, the gate electrode of the third transistor T3 may be formed with the third gate pattern 160A. The source-drain patterns 170A and 170B may be electrically connected to the regions 151 and 153 for firming the source or drain electrode of the thud transistor T3 through the second and third contact holes H2 and H3.

In an exemplary embodiment of the inventive concept, one of the first active pattern 120 and the second active pattern 150 may include an oxide semiconductor, and the other of the first active pattern 120 and the second active pattern 150 may include an inorganic semiconductor. For example, the first active pattern 120 may include the inorganic semiconductor e.g., polysilicon), and the second active pattern 150 may include the oxide semiconductor. Accordingly, the first, second, fifth, and sixth transistors T1, T2, T5, and T6 may be implemented as a polysilicon thin-film-transistor (TFT) of which reliability is relatively high. On the other hand, the third, fourth, and seventh transistors T3, T4, and T7 may be implemented as an oxide TFT in which the leakage current is relatively small. In this case, the gate electrode of the second transistor T2 may receive the first scan signal GS1, and the gate electrode of the third transistor T3 may receive the second scan signal G2 (e.g., an inverted scan signal of a current pixel row) that is an inversion of the first scan signal GS1. In addition, the fourth and seventh transistors T4 and T7 may receive an inverted scan signal of a previous pixel row.

As shown in FIG. 7, the storage capacitor CST may be formed using the first gate pattern 130B and the second gate pattern 140A. Additionally, the first capacitor C1 may be formed using the second gate pattern 140A and the third gate pattern 160A. Thus, the first capacitor C1 may be formed by overlapping the second gate pattern 140A and the third gate pattern 160A to be between the gate electrode of the third transistor T3 and the first power voltage ELVDD. Accordingly, the pixel can reduce the kickback effect caused by the second capacitor C2 (e.g., a parasitic capacitor) between the first gate pattern 130B (e.g., the gate electrode of the first transistor T1) and the third gate pattern 160A (e.g., the gate electrode of the third transistor T3). In an exemplary embodiment of the inventive concept, the first gate pattern 130B does not overlap the third gate pattern 160A in a region in which the first capacitor C1 is formed. Accordingly, not only is the first capacitor C1 is added, but also, the influence of the parasitic capacitor (e.g., the second capacitor C2) is reduced by overlapping the second gate pattern 140A and the third gate pattern 160A. Therefore, the influence of the kickback phenomenon may be efficiently reduced according to [Equation 1] discussed above.

Although FIGS. 5A through 5F, 6, and 7 illustrate an example of implementing the pixel PX-1 of FIG. 2, the pixel PX-1 may be implemented in various ways. For example, the fourth transistor T4 and the seventh transistor T7 may receive different scan signals. Additionally, the first gate pattern 130B may thither overlap the second gate pattern 140A in a region in which the first capacitor C1 is formed to increase a size of the storage capacitor CST.

Figure 8:
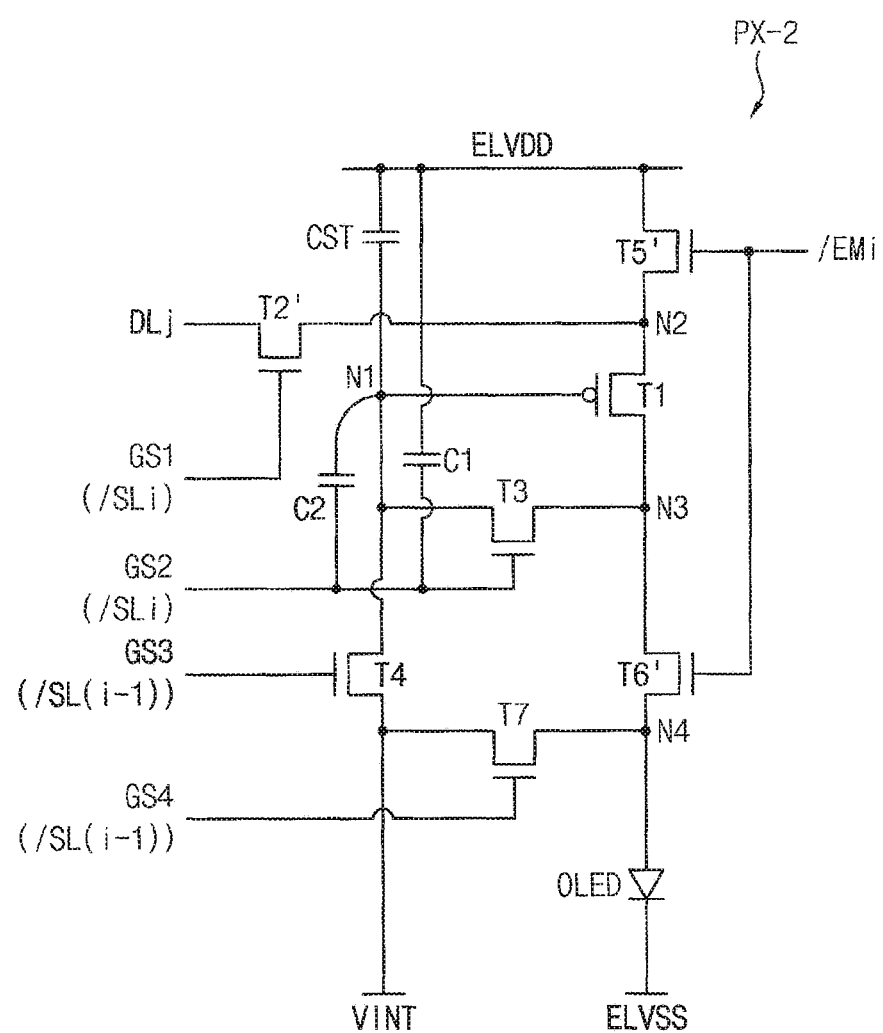
FIG. 8 is a diagram illustrating a pixel included in the organic light emitting display device of FIG. 1 according to an exemplary embodiment of the inventive concept.

FIG. 8 is a diagram illustrating a pixel included in the organic light emitting display device of FIG. 1 according to an exemplary embodiment of the inventive concept.

Referring to FIG. 8, a pixel PX-2 may elude the first, third, fourth, and, seventh transistors T1, T3, T4, and T7, a second transistor T2', a fifth transistor T5', a sixth transistor T6', the storage capacitor CST, the first capacitor C1, the second capacitor C2, and the OLED. The pixel PX-2 according to the present exemplary embodiment is substantially the same as the pixel PX-1 of FIG. 2, except that the second, fifth, and sixth transistors T2', T5', and T6' are n-channel MOS transistors. Therefore, the same reference numerals will be used to refer to the same or like parts as those described with reference to FIG. 2, and any repetitive explanation concerning the above elements will be omitted.

In an exemplary embodiment of the inventive concept the first transistor T1 that is the driving transistor may be a p-channel transistor. On the other hand, the second through seventh transistors T2', T3, T4, T5', T6', and T7 that are switching transistors may be n-channel transistors. Thus, the driving transistor may be implemented as a p-channel MOS transistor to enhance reliability, and the switching transistors may be implemented as n-channel MOS transistors to prevent display quality degradation due to the leakage current. In this case, the second, third, fourth, and seventh transistors T2', T3, T4, and T7 included in the pixel PX-2 of FIG. 8 may be controlled by a scan signal having the same on-level and off-level without an inverted scan signal, unlike the pixel PX-1 in FIG. 2. Therefore, the number of scan lines can be reduced.

Therefore, as described above, each pixel of an organic light emitting display device according to exemplary embodiments of the inventive concept may include a driving transistor that is a p-channel MOS transistor and some switching transistors that are n-channel MOS transistors to prevent a leakage current. Accordingly, the organic light emitting display device can increase reliability of the driving transistor and can prevent display quality degradation caused by the leakage current when the organic light emitting display device is driven at a low frequency.

In addition, the pixel of the organic light emitting, display device includes a first capacitor between a gate electrode of a third transistor and a first power voltage by overlapping a second gate pattern and a third gate pattern to reduce a kickback effect. Accordingly, the organic fight emitting display device can secure a voltage margin for black color data and have increased display quality.

The inventive concept may be applied to any electronic device having an organic light emitting display device. For example, the inventive concept may be applied to a personal computer: a laptop computer, a cellular phone, a smart phone, a smart pad, a personal digital assistant (PDA), etc.

While the inventive concept has been shown and described with reference to exemplary embodiments thereof, it will be apparent to those of ordinary skill in the art that various changes and modifications in form and details may be made thereto without departing from the spirit and scope of the inventive concept as set forth in the following claims.

What is claimed is:

1. An organic light emitting display device, comprising:
a plurality of pixels,
wherein each of the plurality of pixels includes:
an organic light emitting diode (OLED);
a first transistor that includes a gate electrode, a first electrode, and a second electrode, the first transistor being a driving transistor which controls a current flowing into the OLED based on a data signal, the first transistor being a p-channel MOS transistor;
a second transistor that includes a gate electrode receiving a first scan signal, a first electrode receiving the data signal, and a second electrode connected to the first electrode of the first transistor;
a third transistor that includes a gate electrode receiving a second scan signal, a first electrode connected to the second electrode of the first transistor, and a second electrode connected to the gate electrode of the first transistor, the third transistor being an n-channel MOS transistor;
a storage capacitor that includes a first electrode receiving a first power voltage and a second electrode connected to the gate electrode of the first transistor; and
a first capacitor that includes a first electrode connected to the gate electrode of e third transistor and a second electrode receiving the first power voltage.

2. The organic light emitting display device of claim 1, wherein the second transistor is a p-channel MOS transistor.

3. The organic light emitting display device of claim 2, wherein the second scan signal is a signal that is the first scan signal inverted.

4. The organic light emitting display device of claim 1, wherein the second transistor is an n-channel MOS transistor.

5. The organic light emitting display device of claim 1, wherein each of the plurality of pixels further includes:
a fourth transistor that includes a gate electrode receiving a third scan signal, a first electrode receiving an initialization voltage that differs from the first power voltage, and a second electrode connected to the gate electrode of the first transistor, the fourth transistor being an n-channel MOS transistor;
a fifth transistor that includes a gate electrode receiving an emission control signal, a first electrode receiving the first power voltage, and a second electrode connected to the first electrode of the first transistor; and
a sixth transistor that includes a gate electrode receiving the emission control signal, a first electrode connected to the second electrode of the first transistor, and a second electrode connected to a first electrode of the OLED.

6. The organic light emitting display device of claim 5, wherein each of the plurality of pixels further includes:
a seventh transistor that includes a gate electrode receiving a fourth scan signal, a first electrode receiving the initialization voltage, and a second electrode connected to the first electrode of the OLED.

7. The organic light emitting display device of claim 5, wherein the first transistor includes an active pattern having an inorganic semiconductor, and the third and fourth transistors include an active pattern having an oxide semiconductor.

8. The organic light emitting display device of claim 5, wherein the fifth transistor is a p-channel MOS transistor.

9. The organic light emitting display device of claim 5, wherein the fifth transistor is an n-channel MOS transistor.

10. The organic light emitting display device of claim 5, wherein the sixth transistor is a p-channel MOS transistor.

11. The organic light emitting display device of claim 5, wherein the sixth transistor is an n-channel MOS transistor.

12. The organic light emitting display device of claim 5, wherein the seventh transistor is a p-channel MOS transistor.

13. The organic light emitting display device of claim 5, wherein the seventh transistor is an n-channel MOS transistor.

14. The organic light emitting display device of claim 1, wherein each of the plurality of pixels further includes:
 a second capacitor that includes a first electrode connected to the gate electrode of the first transistor and a second electrode connected to the gate electrode of the third transistor.

15. The organic light emitting display device of claim 14, wherein a first capacitance of the first capacitor is larger than a second capacitance of the second capacitor.

16. A pixel, comprising:
 an organic light emitting diode (OLED);
 a first transistor that includes a gate electrode, a first electrode, and a second electrode, the first transistor being a driving transistor which controls a current flowing into the OLED based on a data signal, the first transistor being a p-channel MOS transistor;
 a second transistor that includes a gate electrode receiving a first scan signal, a first electrode receiving the data signal, and a second electrode connected to the first electrode of the first transistor;
 a third transistor that includes a gate electrode receiving a second scan signal, a first electrode connected to the second electrode of the first transistor, and a second electrode connected to the gate electrode of the first transistor, the third transistor being an n-channel MOS transistor;
 a storage capacitor that includes a first electrode receiving a first power voltage and a second electrode connected to the gate electrode of the first transistor; and
 a first capacitor that includes a first electrode connected to the gate electrode of the third transistor and a second electrode receiving the first power voltage.

17. The pixel of claim 16, further comprising:
 a fourth transistor that includes a gate electrode receiving a third scan signal, a first electrode receiving an initialization voltage that differs from the first power voltage, and a second electrode connected to the gate electrode of the first transistor, the fourth transistor being an n-channel MOS transistor;
 a fifth transistor that includes a gate electrode receiving an emission control signal, a first electrode receiving the first power voltage, and a second electrode connected to the first electrode of the first transistor; and
 a sixth transistor that includes a gate electrode receiving the emission control signal, a first electrode connected to the second electrode of the first transistor, and a second electrode connected to a first electrode of the OLED.

18. The pixel of claim 17, further comprising:
 a seventh transistor that includes a gate electrode receiving a fourth scan signal, a first electrode receiving the initialization voltage, and a second electrode connected to the first electrode of the OLED.

19. The pixel of claim 18, wherein the first transistor includes an active pattern having an inorganic semiconductor, and the third and fourth transistors include an active pattern having an oxide semiconductor.

20. The pixel of claim 16, further comprising:
 a second capacitor that includes a first electrode connected to the gate electrode of the first transistor and a second electrode connected to the gate electrode of the third transistor.

* * * * *